United States Patent
Parfitt et al.

(10) Patent No.: US 8,596,462 B2
(45) Date of Patent: Dec. 3, 2013

(54) PARTICLE SEPARATOR

(75) Inventors: Alexander Roy Parfitt, Filton (GB); Ian Michael Sturland, Filton (GB); Clyde Warsop, Filton (GB); Paul James Dawson, Filton (GB)

(73) Assignee: BAE Systems PLC, London (GB)

(*) Notice: Subject to any disclaimer, the term of this patent is extended or adjusted under 35 U.S.C. 154(b) by 1090 days.

(21) Appl. No.: 11/547,668

(22) PCT Filed: Sep. 9, 2005

(86) PCT No.: PCT/GB2005/003466
§ 371 (c)(1),
(2), (4) Date: Oct. 6, 2006

(87) PCT Pub. No.: WO2006/027591
PCT Pub. Date: Mar. 16, 2006

(65) Prior Publication Data
US 2007/0205142 A1 Sep. 6, 2007

(30) Foreign Application Priority Data
Sep. 10, 2004 (GB) .................................. 0420292.5

(51) Int. Cl.
*B07B 4/00* (2006.01)
(52) U.S. Cl.
USPC .................... 209/139.1; 209/142; 209/143
(58) Field of Classification Search
USPC ................. 209/138, 139.1, 142, 143
See application file for complete search history.

(56) References Cited

U.S. PATENT DOCUMENTS

| | | | |
|---|---|---|---|
| 3,001,914 A | 9/1961 | Andersen | |
| 3,693,457 A * | 9/1972 | Pilat | 73/865.5 |
| 3,938,366 A | 2/1976 | Wertlake et al. | |
| 4,524,748 A | 6/1985 | Giannotti | |
| 4,640,140 A * | 2/1987 | Burghoffer et al. | 73/863.22 |
| 4,972,957 A * | 11/1990 | Liu et al. | 209/143 |

(Continued)

FOREIGN PATENT DOCUMENTS

| | | |
|---|---|---|
| EP | 0 964 240 A1 | 12/1999 |
| EP | 1 126 021 A1 | 8/2001 |
| EP | 1 233 056 A1 | 8/2002 |

OTHER PUBLICATIONS

International Preliminary Report on Patentability and attached Written Opinion (Forms PCT/IPEA/416 and PCT/IPEA/409), mailed Jan. 19, 2007 in corresponding PCT Application No. PCT/GB2005/003466, European Patent Office, Rijswijk, The Netherlands.

(Continued)

*Primary Examiner* — Joseph C Rodriguez
(74) *Attorney, Agent, or Firm* — Buchanan Ingersoll & Rooney PC (57) ABSTRACT

A separator is disclosed for separating particles of at least first and second mass/size ranges from an ambient fluid (e.g. gaseous) medium in which they are present, particles of the first range being of generally larger size/mass than particles of the second range. The separator is especially designed for use in an air monitoring device which is designed for rapid detection of micro-organisms such as bacteria, viruses, pathogens and the like, and is designed to be portable so that it can be readily and rapidly deployed in both civilian and military environments and can be used indoors and outdoors; it can also be designed for personal use.

17 Claims, 7 Drawing Sheets

(56) References Cited

U.S. PATENT DOCUMENTS

| | | | |
|---|---|---|---|
| 6,342,388 | B1 | 1/2002 | Van Den Wildenberg |
| 6,402,817 | B1 | 6/2002 | Bergman |
| 6,431,014 | B1 * | 8/2002 | Liu et al. ............... 73/863.22 |
| 6,688,187 | B1 | 2/2004 | Masquelier |
| 6,786,105 | B1 * | 9/2004 | Sioutas ................. 73/863.22 |
| 6,938,777 | B2 * | 9/2005 | Call et al. .................. 209/143 |
| 7,082,811 | B2 * | 8/2006 | Marple et al. ............ 73/28.05 |
| 2004/0016680 | A1 | 1/2004 | Call et al. |

OTHER PUBLICATIONS

Huang et al, "Continuous Particle Separation Through Deterministic Lateral Displacement", Science, May 14, 2004, pp. 987-990.

Marple et al, "Virtual Impactors: A Theoretical Study", Environmental Science & Technology by the American Chemical Society, Aug. 1980, pp. 976-985.

* cited by examiner

PARTICLE SEPARATOR

FIELD

This invention is concerned with particle separators and is particularly concerned with devices for monitoring the presence of selected particles in fluids, both liquid and gases, and in particular though not exclusively for monitoring air constituents. The invention is more especially concerned with such devices that are capable of monitoring ambient air to detect for the presence of chemical and biological agents present in the air.

BACKGROUND

It is perceived that there is a current and urgent need for air-monitoring devices that are easy to operate, can be manufactured in large quantities, can detect and identify as many hazardous agents in the atmosphere as possible, and are highly portable so that they can be readily and easily deployed wherever and whenever required and can be highly responsive to the presence of selected particles both in the open air and inside buildings, in mass transport vehicles such as aircraft, ships, trains and buses as well as being available for personal use. It is also a requirement that such devices can identify these hazardous agents within a sufficiently short time frame that remedial action can be taken before they can have any serious effect, both in the military and non-military environments.

Previous proposals have been put forward to provide particle separation for particles as small as the sub-micron level (see for example "Particles separate doing the Tango" Biotechnology July 2004, "Continuous Particle Separation Through Deterministic Lateral Displacement" by L. R. Huang et al. Science, May 14, 2004). A further study, among others, is to be found in "Virtual Impactors: A Theoretical Study" by V. A. Marple & C. M. Chien published 1980 in Environmental Science & Technology by the American Chemical Society.

Whilst such separators are known and have been proposed for separating extremely small particles, they are not suitable as separators of monitoring devices which are required for the separation and identification of microbial or bacteriological or like particles, and are not readily deployable in numbers.

The fundamental reason for this is that known particle separators are substantial, can only deal with small volumes of air or other gases in a given time frame and are primarily concerned with separation, but not necessarily with the preservation of the integrity of, the particles so separated, so that a pathogen, virus, germ or the like can be subsequently identified, due to collision of such particles as they are being separated and collected. Indeed, in the prior art, collision is identified as a definite result of the structure and operation of the separator.

Collision may occur in the particle stream or with walls of known separators, or both. If this occurred in separating bacteria and the like, the ability to identify that bacterium would be seriously impaired due either to damage to the bacterium, thereby potentially altering its own structure, or due to cross contamination. Consequently, known particle separators are unsuitable for use in separating and collecting particles which can be damaged by impact.

We have therefore developed a particle separator in which the potential risk of such damage is minimised. This has been achieved by analysis of a range of bacteria, viruses etc. as to size and mass, and an understanding of the optimisation of the air flow which will permit separation of such particles without any significant collision between them.

Generally speaking, in ambient air, particles exist that are of a range of less than 50 microns. Larger particles in the atmosphere generally tend to settle and do not remain in the atmosphere. Below the 50 micron level, atmospheric particles can usually be classified into three size ranges, namely 20-50 microns, 2-20 microns and below 2 microns. Micro-organisms such as bacteria, germs, viruses and the like are normally considered to be at the lower end of the overall range, though some noxious and poisonous materials may exist in the sub 40 micron, and in particular the 2-20 micron, range. For this reason, it may also be advantageous to consider the centre range as comprising more than one 'sub-range'. For a separator of a 'universal' detector of chemical and/or biological agents, it is most important that as many pathogenic and/or toxic substances are detected as is possible, which is to say without damage thereto such as would remove the ability to identify them.

BRIEF SUMMARY

To this end, the present invention provides a separator for separating particles of first and second mass/size ranges from an ambient fluid medium in which they are present, particles of the first range being of generally larger size/mass than particles of the second range, the separator comprising a body having an inlet provided by a plurality of inlet ports through which the ambient fluid medium can be admitted into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator.

The present invention further provides a separator for separating particles of first and second mass/size ranges from an ambient gaseous medium in which they are present, particles of the first range being of generally larger size/mass than particles of the second range, the separator comprising a body having an axis and an axial inlet provided by a plurality of inlet ports through which the gaseous medium can be drawn into the separator, each inlet port leading to a respective first chamber having a plurality of outlet ports around its periphery leading from the chamber and through which particles of the second range can be drawn during operation of the separator for subsequent collection, while particles of the first range pass generally axially through the chamber, each chamber having an outlet, remote from its inlet, through which outlet particles of said first range can be vented from the separator.

It is to be noted that the ambient gaseous medium, most commonly air, is drawn into the separator and not blown, which, with the arrangement of the inlet ports, chamber and channels and the control of the rate at which air is drawn into the separator, minimises the possibility of particle (e.g. bacterium) collision.

A preferred monitoring device, including a separator according to the present invention, is designed to be portable and to accommodate a flow rate of air through the monitoring device of approximately 200 litres/min., this being considered as adequate to sample ambient air both in a battlefield environment and in the civilian environment.

To effect this air flow, the monitoring device, which is ideally of but not limited to a cylindrical shape, is of a diameter of approximately 100 mm, and so can be readily held in the hand. It will be readily understood that a separator according to the present invention can be constructed so as to be of any convenient shape and size and that it need not be of cylindrical shape.

In the preferred embodiment described hereinafter with reference to the accompanying drawings, the ports of the plurality of inlet ports are generally of substantially similar size and shape and are arranged concentrically around the axis. It will be readily appreciated that, although in the illustrated embodiment, the inlet ports are so arranged and sized, this is predominantly a design consideration and therefore the ports can be arranged otherwise and their respective sizes, dimensions (i.e. cross-sections, length etc.) and positions relative to one another can be varied according to requirements regarding the size and/or mass of particles to be collected.

Preferably, each chamber has an axis parallel to the axis of the container and the outlet ports around the periphery of each chamber are arranged in concentric arrays about the respective chamber axis; the concentric arrays of outlet ports are preferably arranged in an annular gallery above a floor area of the respective chamber.

Each of the outlet ports may be provided by a passageway leading to an annular space formed beneath the gallery, the annular space being isolated from the chamber. One or more ducts leads from the annular space and is/are arranged for alignment and connection with a particle collector when the separator is connected thereto.

A second annular space is, in a preferred embodiment of the invention, provided beneath said annular space, and said second annular space is then connected to said annular space whereby particles can pass from said annular space to said second annular space, said second annular space having outlets therefrom whereby said particles can be directed to said particle collector when the separator is connected thereto.

The particles of said second range will preferably include particles of discrete third and fourth size/mass ranges where particles of the third range are of greater size/mass than the fourth range, the separator being capable of extracting particles of the fourth range in said annular space and particles of the third range proceeding to the second annular space.

In a further separator according to the invention, a plurality of annular spaces may be provided beneath said second annular space, each annular space of said plurality thereof being then connected to an immediately upper annular space whereby particles can pass from said immediately upper annular space thereto, and each annular space having outlets therefrom whereby said particles can be directed to said particle collector when the separator is connected thereto. Each of the inlet ports has a floor and a lowermost one of said plurality of annular spaces will then be connected with an aperture leading to an outlet beneath said floor.

Particles of the fourth range can be separated from particles of the third range is provided by separating said annular space into a first annular space and a second annular space with a partition therebetween such that the second annular space is separated from the outlet ports by the first annular space, the first annular space having an exit which is transverse to the axis of the respective chamber and through which particles of the fourth range can be drawn for collection, while the particles of the third range are directed through further outlets for separate collection.

The present invention also provides a monitoring device for use in monitoring contaminants and other particles in air, the monitoring device comprising a separator according to the present invention, a particle detector coupled to the separator and means for drawing air through the separator for collection by the particle detector.

Such a device is ideally portable and may be wall-mountable. It also may include means for drawing air through the separator. Such means is preferably a battery driven fan though where proposed to be used in a fixed installation (e.g. one in which it will be used to monitor air content on a long term basis), it may be connected to a power source such as a mains source of electricity. A monitoring device according to the present invention may also be adapted for use by an individual wearer such as military personnel, medical personnel or security personnel and for such purpose can be fitted with a clip or the like whereby it can attached to a belt.

The present invention further provides a method of making a separator according to the invention which comprises fabricating the separator from a plurality of wafers which are laminated together. Alternatively, a separator according to the invention could be manufactured from suitable plastics material by, for example, laser drilling.

DESCRIPTION OF THE DRAWINGS

Additional features of the invention will become apparent from the following description of an embodiment of the invention which is illustrated by way of example in the accompany drawings, in which.

DETAILED DESCRIPTION

Figure 1:
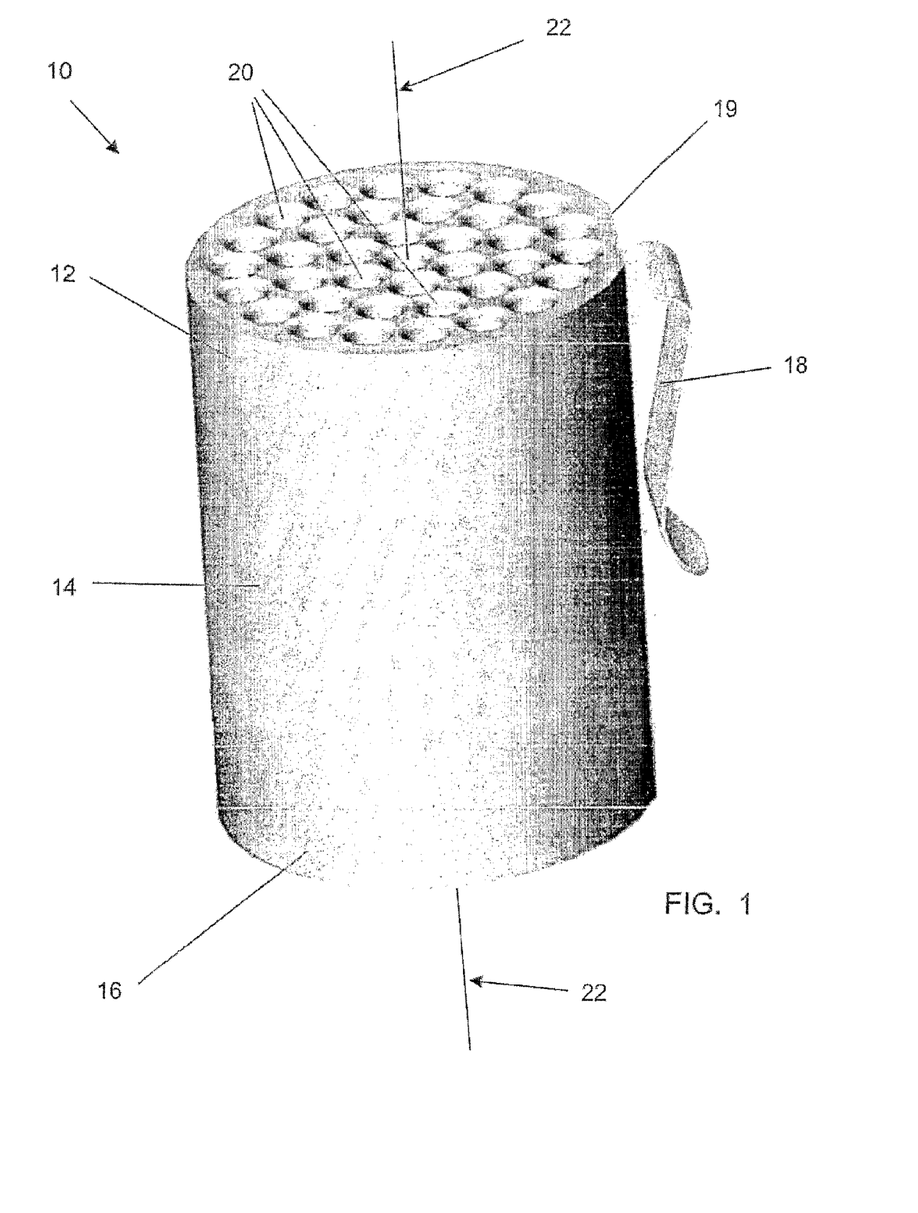
FIG. 1 is a perspective view of an air monitoring device which includes a particle separator according to the invention.

Referring firstly to FIG. 1, there is shown therein a portable air-monitoring device 10 which incorporates a particle separator 12 according to the present invention. The device 10 is substantially cylindrical (though, as previously mentioned, this is not essential) and comprises the separator 12 providing an upper section of the device 10, a second or central section 14 in which are provided means for operating the device and for collecting and analysing the collected particles from the surrounding atmosphere, and a third or base section 16 in which a fan is mounted for drawing air through the device 10 when it is operated. Though of substantially cylindrical shape, the illustrated device has a flat 19 and the central section 14 has a clip 18 secured to the flat whereby the device can be attached to a wearer's belt or clothing or by which it can be mounted on a wall or other appropriate fixing.

The present invention is primarily concerned with the upper section 12 providing the separator.

The separator 12 is intended, as discussed above, for use in separating particles from the atmosphere into the three cited size ranges, which, at the particle types and sizes under consideration, equates closely to the respective mass ranges of those particles. It will be clearly understood that, though the illustrated embodiment is hereinafter described with respect to particle size, the invention is equally useful in separating particles by reference to their mass or by reference to both mass and size.

Figure 2:
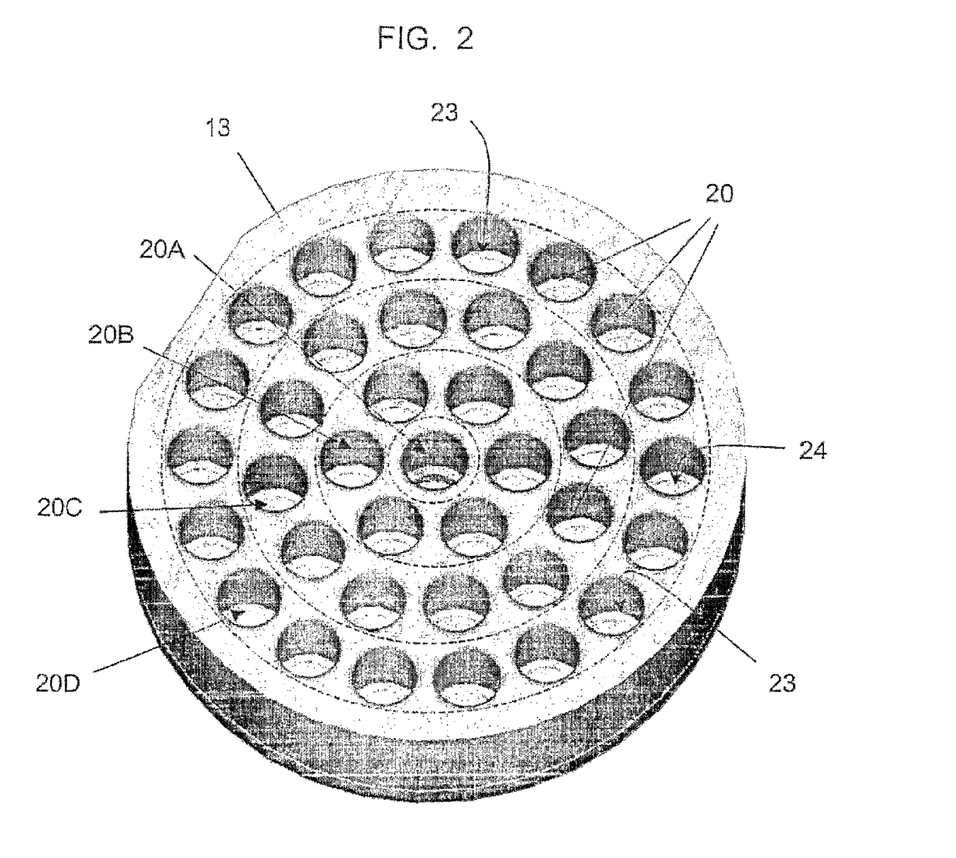
FIG. 2 is a more detailed perspective view of the separator shown in FIG. 1.
Figure 3:
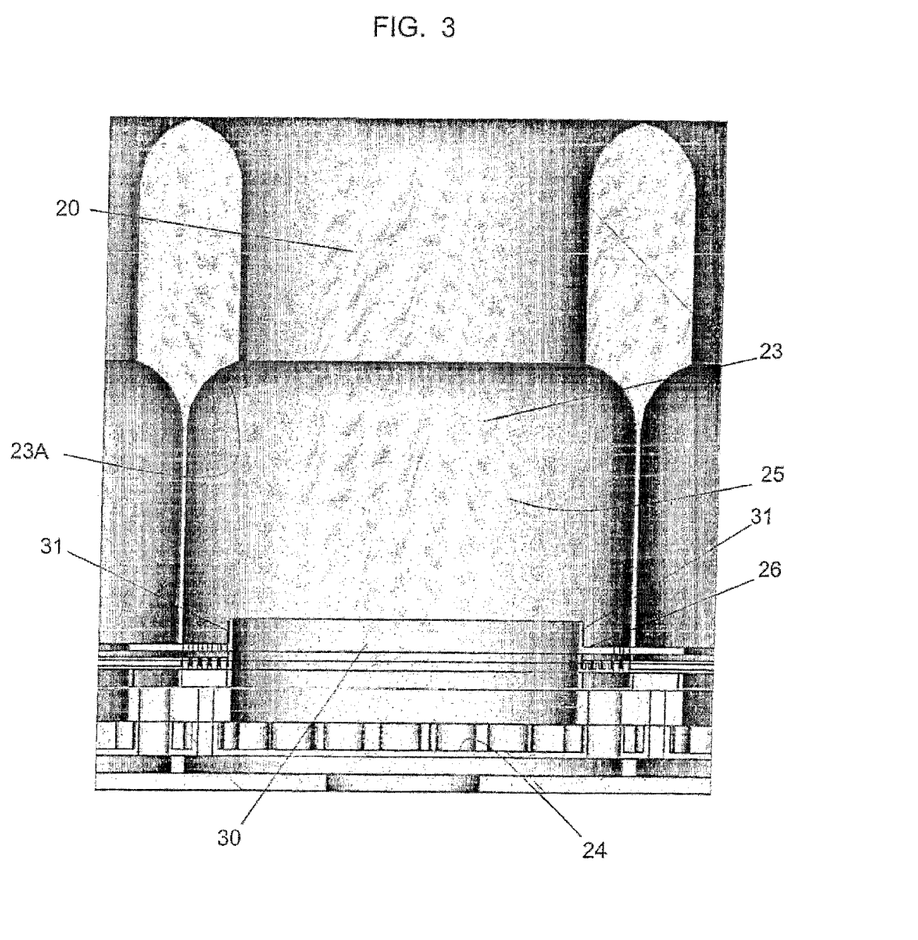
FIG. 3 is a partially cutaway perspective view of the upper section of the separator.
Figure 8:
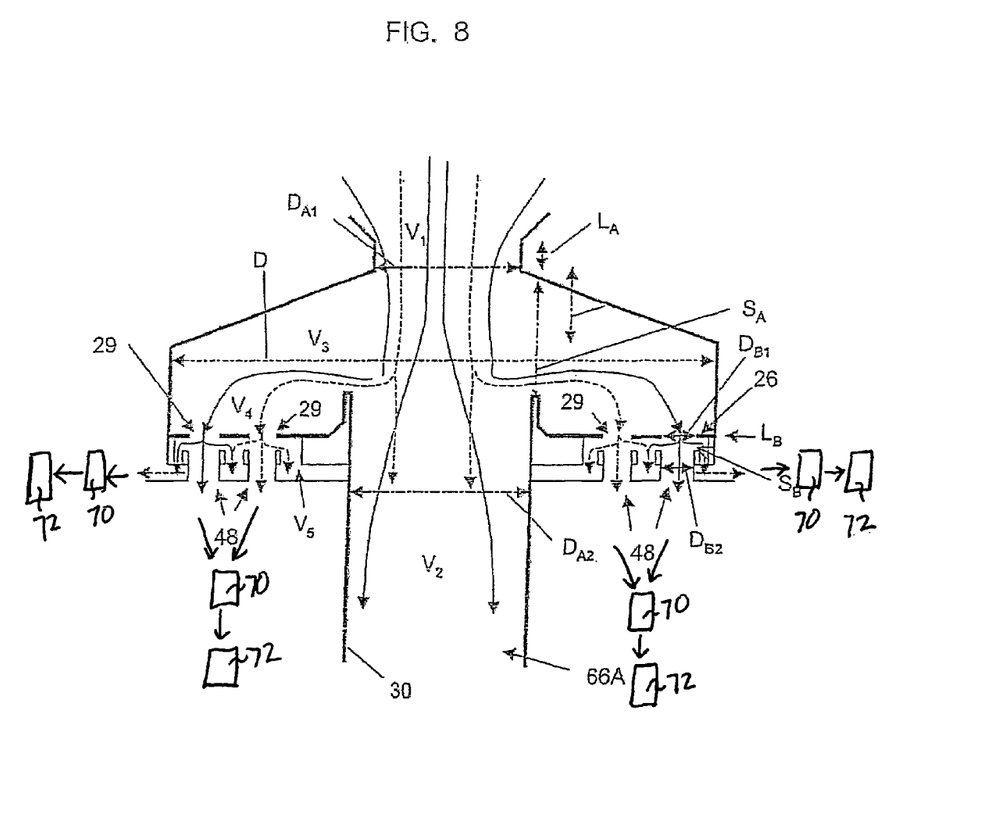
FIG. 8 is a schematic diagram showing air flow through the separator.

The separator 12 of the illustrated embodiment is in the form of a body 13 which has a plurality of inlet ports 20. In the illustrated embodiment, there are thirty-seven. The device, and therefore the separator has a general axis 22, as shown in FIG. 1, and the ports are arranged around a central port 20A (FIG. 2) in three concentric arrangements 20B, 20C and 20D, with six ports in the innermost circle 20B, twelve ports in the intermediate circle 20C, and eighteen ports in the outermost circle 20D. In FIG. 2, these concentric arrangements of the ports are indicated by dotted lines. (In alternative embodiments of the invention, it is not necessary that the ports be so arranged. It is important though that the arrangement of the ports optimises the ability of the plurality of ports to take in the airflow that is desired.) Each port is of substantially cylindrical shape but tapering very slightly with the depth of the port and is formed as a recess in the body 13 of the separator, with its cylinder axis (not shown) parallel to the axis 22. Referring also to FIG. 8, which is a diagrammatic representation of the construction and arrangement of the separator and approximates to FIG. 4, it will be seen that each port 20 has a depth $L_A$ and a diameter $D_{A1}$ at its lower extremity and leads to a chamber 23 which is of a larger diameter D than the port 20 and has an annular open roof 23A FIG. 3) which has the shape of a frustum of a sphere descending to a substantially cylindrical wall 25. The chamber 23 has a floor 24 and above the floor is formed a gallery 26 provided by an annular plate-like structure 28 in which are formed five concentric circles of outlet ports 29. In the illustrated embodiment, there are of the order of six hundred and fifty-seven such outlet ports in each structure 28. Thus, the thirty-seven inlet ports provide a total of some 24,309 outlet ports 29, each having a diameter $D_{B1}$ and a depth $L_B$ (see FIG. 8). It will be appreciated that the exact number of these ports and their size and depth will be dependent upon the size or mass of particle(s) to be separated at this and subsequent stages of the separator and the velocity of the particles being drawn into the separator.

In a portable device as shown in FIG. 1, designed for separating particles of a size not exceeding about 20 microns from ambient air, and for subsequently separating those particles into sub-groups, the external diameter of the device is approximately 100 mm, and the internal diameter $D_{A1}$, of each inlet port 20 is 10.27 mm while the internal diameter $D_{B1}$ of each outlet port 29 is 183 μm. We have determined that with such dimensions, it is possible to induce a flow rate of about 185 to 200 litres per minute through the device under the desired conditions as discussed below.

Radially outwardly, the gallery 26 is bounded by the annular wall 25 defining the periphery of the chamber 23, while radially inwardly, the gallery is bounded by a continuous curtain wall 30 which descends from the plane of the gallery 26 and terminates at a height above the floor 24 which is approximately one-third of the vertical separation of the gallery 26 from the floor 24. At the top of the curtain wall, an upwardly-projecting rim 32 is provided.

Behind the curtain wall (i.e. radially outwardly of the curtain wall) and beneath the gallery 26, an annular space 34 is formed which is isolated from the chamber 23 by the curtain wall, the annular space 34 having an annular base 36 which is integral with the outer body 13 of the device 10. The upper surface 38 of the annular base 36 is located approximately midway between the top and bottom of the curtain wall 30 and is of a thickness such that it extends to the bottom of the curtain wall.

The annular space 34 between the gallery 26 and the surface 38 is separated into a first, upper, annular space 40 and a second, lower, annular space 42 by an annular intermediate floor 44. This annular floor provides a partition between the two annular spaces 40 and 42 and has a plurality of further outlets 48 provided by apertures 50 formed in the annular floor 46, the apertures each having upward chimney-like extensions 52 each of which has an internal diameter $D_{B2}$ (see FIG. 8) and is spaced from the underside of the gallery 26 by a distance $S_B$. There are as many apertures 50 and associated extensions 52 as there are outlets 29, the apertures 50/extensions 52 being axially aligned with the outlets 29.

Figure 6:
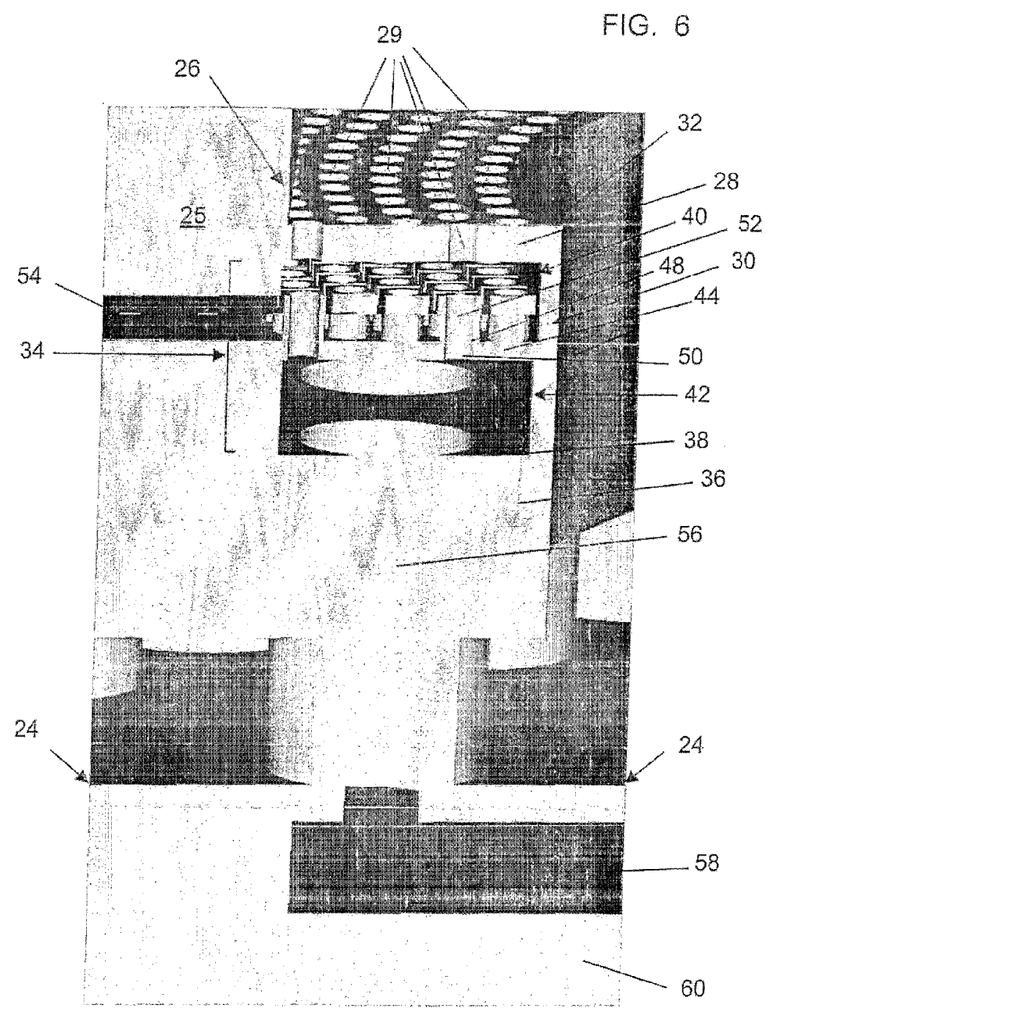
FIG. 6 is a cut-away part-sectional view of the separator.

Extending radially outwardly from the first annular space 40 is a plurality of ducts 54 (FIGS. 4 and 6), only one of which is shown in FIG. 6. These ducts, as explained below, lead to a particle collector 70 which is provided in the control section 14 of the device 10. The particle collector 70 does not per se form an essential integer of the present invention and will therefore not be further described.

Figure 4:
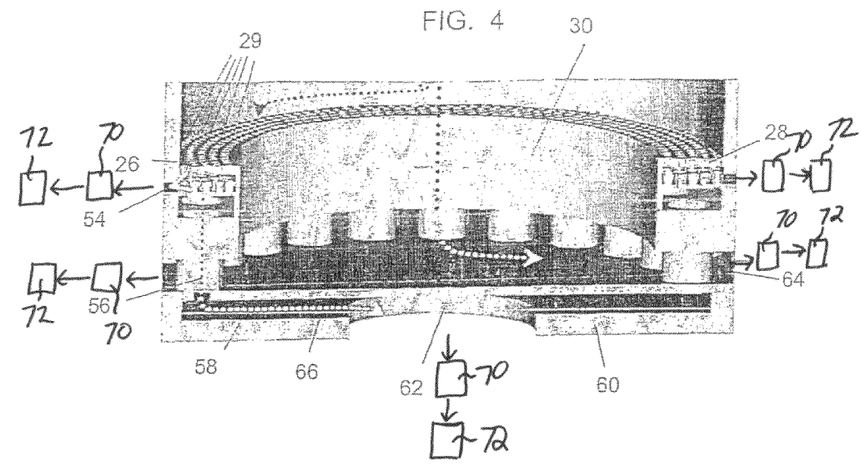
FIG. 4 is a plan view of an upper section of the separator shown in FIG. 2.
Figure 5:
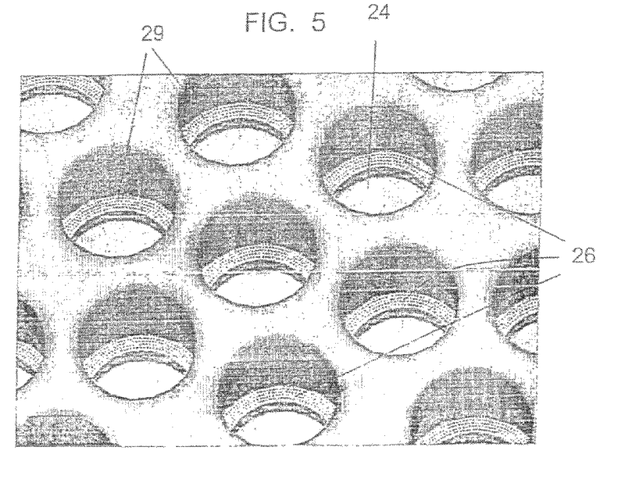
FIG. 5 is a more detailed perspective view of the upper section of the separator.

Extending downwardly from the annular upper surface 38 of the annular base 36, and through the base is a plurality of cylindrical shafts 56 having axes parallel to the axis 22. These shafts connect with a shallow, cylindrical space 58 which is formed between the underside of the floor 24 and an underfloor 60 which has a central aperture 62 formed therein. As shown in FIG. 4, this central aperture 62 which, it will be recalled, is one of thirty-seven such apertures, leads to the aforementioned particle collector.

Figure 7:
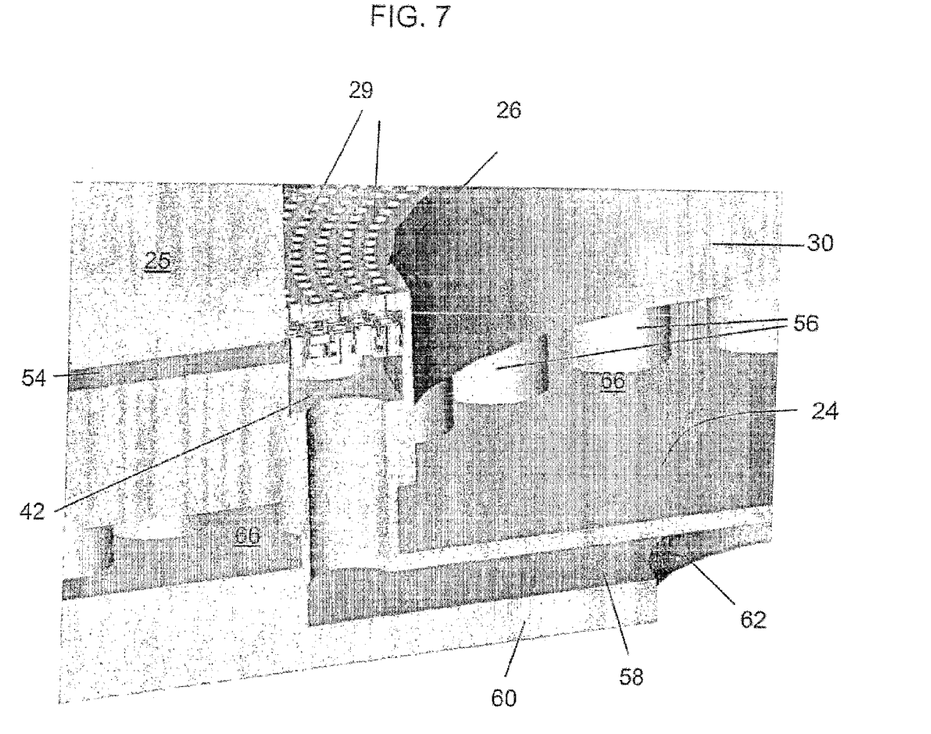
FIG. 7 is a close-up cut-away part sectional view of the separator.

The lower part of the chamber 23 is bounded by an annular colonnade 64 of the shafts 56 (FIGS. 4, 6 and 7), defining gaps 66 between adjacent columns. The spacing defining the gaps 66 extends through to similar spacing beneath each of the thirty-seven inlet ports 20, thereby providing a unitary space which, though not shown, can be coupled to exhaust or to the particle collector of the device, as required.

The function and operation of the separator is as follows:

Inertial mass is used to separate a single stream of particles into two streams depending upon their weight. Large particles will continue in a forward direction whilst smaller, lighter particles are drawn off to the side. The principle of this is shown in FIG. 8.

Air is drawn into and through the device by operation of suction means 72 which in the present embodiment of the invention is a battery-operated fan mounted in the base section 16 of the device. The fan is able to draw air into the device via ducts (not shown) leading to the fan from the particle separator and which may or may not bypass the particle collector 70 mounted in the central section 14 of the device. The manner in which air is drawn through the central and base sections of the device is not central to the present invention and will not therefore be further described.

Of course, the particle collector 70 itself is connected with the radial ducts 54 and with the central aperture 62, and so air is drawn through them as from the colonnaded spacing 66 between the shafts 56.

Air enters the device 10 through the ports 20, and as shown schematically in FIG. 8. The air is drawn down through the outlets 29 and through the space 66. Air passing into the space 66 can be drawn off to exhaust. On the other hand, air passing through the outlets 29 enters the first annular space 40 below the gallery 26 and, depending upon particle size, is either drawn off through the radial ducts 54 or passes through the extensions 52 into the second annular space 42 beneath the intermediate floor structures 44, from where it is drawn into the central aperture 62. Air drawn through the ducts 54 and the aperture 62 is conducted to the particle collector.

The design, geometry and proportions of the separator are calculated such that only particles of given size ranges are collected. Thus, for example, with the illustrated embodiment, particles of a size, of say less than 20 microns, and which are drawn into the separator with a given inertia, which is dependent partly on the speed of the fan, are more readily influenced by the suction effect of the fan than larger sized particles, which proceed under their own momentum, as shown in FIG. 8. If the separator was designed to separate particles according to their mass only, then similar considerations would apply.

The suction effect of the fan is exerted through the outlets 29 and through the space 66. This is represented schematically in FIG. 8 by the passages 29 and the vertical passage 66A. As can be seen from FIG. 8, heavier particles, in the upper range of particle size/mass, continue to flow in approximately the same direction as they enter the separator while lighter particles, in the lighter size/mass range, are drawn off through the passages 29. Some particles at the upper end of the lighter mass range may continue along the passage 66A but the much larger proportion will be drawn into the passages 29. Provided that sufficient quantities of such particles are drawn off into the passages to permit the collector 70 to detect their presence and allow identification, the precise quantity of particles is not important.

The lighter particles can then, in a subsequent separation, themselves be further separated into sub-ranges in one or more further separation stages.

The separation of the particles is determined initially by the internal diameter $D_{A1}$ of each of the inlet ports 20, which, for the particle separation with which the present invention is primarily concerned, we have determined should be a maximum of 12 mm at its entrance, tapering to a minimum diameter of 10.27 mm. With these magnitudes, we have determined that 95% of the airflow will continue in the major flow and be channelled into the particle separator for subsequent separation and analysis.

The depth $L_A$ (FIG. 8) of the inlet ports together with the overall total area of the outlets (each it will be remembered is of diameter $D_{B1}$) represented by the passages 29 is also determinative in assuring that the flow of air is as desired. It will be readily appreciated that the airflow as represented will be similar for each outlet 29, though this is not necessarily always so and depends upon the types and nature of particles to be separated. At the inner edge of the gallery 26 is a perimetral rim or wall 31 (shown in FIG. 3 and in exaggerated form in FIG. 8 but omitted from the remaining Figures for the purposes of clarity only) which is of a height such that the vertical separation $S_A$ of the wall 31 from the roof 23A permits particles of the correct size (i.e. the range(s) of sizes of interest) to be entrained to enter the outlet ports 29. Without the provision of the wall 31, it is possible that particles could collide with the upper edge of the curtain wall 30 and be adversely affected and yet still be entrained to flow into the outlets 29. Provision of the wall 31 prevents this from occurring.

The dimension $D_{A2}$, which represents the cross-sectional area through which air which is not to be analysed is allowed to vent to atmosphere, is such as to allow its unrestricted dispersion.

Particles are drawn into the separator 10 at a velocity $V_1$ and as they enter the larger volume of the chamber 23, those particles which descend to the floor of the chamber acquire a velocity $V_2$ while those which veer towards the outlet ports 29 acquire a velocity $V_3$. As the latter particles enter the outlet ports 29, the velocity changes to a velocity $V_4$ and those particles that pass through the apertures 50 and the extensions 52 maintain this velocity while those which are diverted into the upper space 40 acquire a velocity $V_5$.

Fabrication of the separator is essentially by forming elements of the separator from a sequence of wafers made from inert material such as silicon dioxide and assembling the wafers in the appropriate sequence.

It will be clearly understood from the foregoing description that although the invention has been described with reference to a separator having provision for separation of airborne particles into three size/mass ranges, the invention can be readily developed to provide for separation of more than three ranges by increasing the number of separation points. For example, by appropriate changes to the geometry of the outlets shown in FIG. 6 and addition of one or more levels corresponding to the annular spaces 40 and 42 (with their appropriate inlets and outlets), it will be possible to effect separation of airborne particles into a significantly larger number of separation stages while, with the method of fabrication used, retaining the portable characteristics of the monitoring device of which it will form a part. In addition, with the correct geometries, a separator according to the present invention can be readily adapted to separate liquids and particles present in liquids.

Furthermore, depending upon the environment and conditions in which a separator, as part of a monitoring and detection device, might be used, the device itself may be enclosed within a protective container.

The invention claimed is:

1. A separator for separating particles of first and second mass/size ranges from an ambient fluid medium in which they are present, particles of the first range being of generally larger size/mass than particles of the second range, the separator comprising a body having an inlet provided by a plurality of inlet ports through which the ambient fluid medium can be admitted into the separator, each inlet port leading to (i) a respective first chamber; (ii) a respective set of a plurality of outlet ports, around the periphery of the chamber leading from the chamber, and; (iii) an outlet from the chamber, the outlet being remote from the inlet of the chamber wherein during operation of the separator particles of the second range can be drawn through the plurality of outlet ports for subsequent collection, while particles of the first range pass generally axially through the chamber to be vented from the separator via the outlet, and wherein a predetermined pressure variation at the ports is provided to permit the particles to be directed in dependence upon the inertial mass of said particles, thereby enabling the particles to be separated by the separator without there being a significant physical contact with the particles and wherein each inlet port is associated with an individual arrangement of features (i), (ii) and (iii).

2. A separator for separating particles of first and second mass/size ranges from an ambient gaseous medium in which they are present, particles of the first range being of generally larger size/mass than particles of the second range, the separator comprising a body having an axis and an axial inlet provided by a plurality of inlet ports through which the gaseous medium can be drawn into the separator, each inlet port leading to a respective first chamber; (ii) a respective set of a plurality of outlet ports around the periphery of the chamber leading from the chamber, and; (iii) an outlet fro the chamber, the outlet being remote from the inlet of the chamber wherein during operation of the separator particles of the second range can be drawn through the plurality of outlet ports for subsequent collection, while particles of the first range pass generally axially through the chamber to be vented from the separator via the outlet, and wherein a predetermined pressure variation at the ports is provided to permit the particles to be directed in dependence upon the inertial mass of said particles, thereby enabling the particles to be separated by the separator without there being a significant physical contact with the particles and wherein each inlet port is associated with an individual arrangement of features (i), (ii) and (iii).

3. The separator according to claim 1 wherein the ports of the plurality of inlet ports are of substantially similar size and shape and are arranged concentrically with a substantially common orientation.

4. The separator according to claim 2 as appended thereto wherein each chamber has an axis parallel to the axis of the container and the outlet ports around the periphery of each chamber are arranged in concentric arrays about the respective chamber axis.

5. The separator according to claim 4 wherein the concentric arrays of outlet ports are arranged in an annular gallery above a floor area of the respective chamber.

6. The separator according to claim 5 wherein each of the outlet ports is provided by a passageway leading to an annular space formed beneath the gallery, the annular space being isolated from the chamber.

7. The separator according to claim 6 wherein one or more ducts leads from the annular space and is/are arranged for alignment and connection with a particle collector when the separator is connected thereto.

8. The separator according to claim 7 wherein a second annular space is provided beneath said annular space, and said second annular space is connected to said annular space whereby particles can pass from said annular space to said second annular space, said second annular space having outlets therefrom whereby said particles can be directed to said particle collector when the separator is connected thereto.

9. The separator according to claim 1 wherein the particles of said second range include particles of discrete third and fourth size/mass ranges where particles of the third range are of greater size/mass than the fourth range, the separator being capable of extracting particles of the fourth range in said annular space and particles of the third range proceeding to the second annular space.

10. The separator according to claim 8 wherein a plurality of annular spaces is provided beneath said second annular space, each annular space of said plurality thereof being connected to an immediately upper annular space whereby particles can pass from said immediately upper annular space thereto, and each annular space having outlets therefrom whereby said particles can be directed to said particle collector when the separator is connected thereto.

11. The separator according to claim 10 wherein each of the inlet ports has a floor and a lowermost one of said plurality of annular spaces is connected with an aperture leading to an outlet beneath said floor.

12. The separator according to claim 8 as appended thereto wherein the particles of the fourth range can be separated from particles of the third range is provided by separating said annular space into a first annular space and a second annular space with a partition therebetween such that the second annular space is separated from the outlet ports by the first annular space, the first annular space having an exit which is transverse to the axis of the respective chamber and through which particles of the fourth range can be drawn for collection, while the particles of the third range are directed through further outlets for separate collection.

13. A monitoring device for use in monitoring contaminants and other particles in air, the monitoring device comprising:

a separator having a body having an inlet provided by a plurality of inlet ports through which the ambient fluid medium can be admitted into the separator, each inlet port leading to (i) a respective first chamber; (ii) a respective set of a plurality of outlet ports around the periphery of the chamber leading from the first chamber, and (iii) an outlet from the chamber, the outlet being remote from the inlet of the chamber, wherein during operation of the separator particles of the second range can be drawn through the plurality of outlet ports for subsequent collection, while particles of the first range pass generally axially through the first chamber, to be vented via the outlet from the separator, and wherein a predetermined pressure variation at the ports is provided to permit the particles to be directed in dependence upon the inertial mass of said particles, thereby enabling the particles to be separated by the separator without there being a significant physical contact with the particles and wherein each inlet port is associated with an individual arrangement of features (i), (ii) and (iii);

a particle detector coupled to the separator; and means for drawing air through the separator for collection by the particle detector.

14. The monitoring device according to claim 13 which is portable.

15. The monitoring device according to claim 13 wherein means is provided for drawing air through the separator.

16. The monitoring device according to claim 15 wherein said means is provided by a battery driven fan.

17. The method of making a separator according to claim 1 which comprises fabricating the separator from a plurality of wafers which are laminated together.

* * * * *